United States Patent [19]

Manley et al.

[11] Patent Number: 4,804,658

[45] Date of Patent: Feb. 14, 1989

[54] IMIDAZOPYRIDINE DERIVATIVES AND PHARMACEUTICAL COMPOSITIONS

[75] Inventors: Paul W. Manley, Monks Risborough; Roderick A. Porter, High Wycombe, both of United Kingdom

[73] Assignee: G. D. Searle & Co., Chicago, Ill.

[21] Appl. No.: 908,126

[22] Filed: Sep. 15, 1986

[51] Int. Cl.[4] .................. A61K 31/44; A61K 31/535; C07D 471/04

[52] U.S. Cl. ................... 514/234.2; 514/183; 514/210; 514/211; 514/212; 514/228.5; 514/303; 540/467; 540/481; 540/544; 540/347; 544/58.4; 544/127; 546/118

[58] Field of Search ............... 540/467, 48, 544, 547; 544/58.4, 127; 546/118; 514/183, 210, 211, 212, 228.5, 234.2, 303

[56] References Cited

PUBLICATIONS

Deutsche–Gold, *Chemical Abstracts*, vol. 83 (1975), No. 10080d.

*Primary Examiner*—Robert W. Ramsuer
*Attorney, Agent, or Firm*—J. Timothy Keane; Paul D. Matukaitis

[57] ABSTRACT

This invention relates to novel imidazopyridine derivatives useful in the treatment of diseases or disorders mediated by platelet-activating factor. This invention further relates to pharmaceutical compositions of such imidazopyridine derivatives.

87 Claims, No Drawings

IMIDAZOPYRIDINE DERIVATIVES AND PHARMACEUTICAL COMPOSITIONS

BACKGROUND OF THE INVENTION

Platelet-activating factor (PAF) has been associated with various biological activities and pathways, thus making it an important mediator responsible for a variety of physiological processes including, but not limited to, activation or coagulation of platelets, smooth muscle contraction, pathogenesis of immune complex deposition, inflammation, and respiratory, cardiovascular and intravascular alterations. These physiological processes are associated with a large group of diseases, such as, for example, cardiovascular disorders, asthma, lung edema, endotoxin shock, adult respiratory distress syndrome and inflammatory diseases.

European Patent Application Nos. 142,333 and 142,801 disclose a class of glycerol derivatives and indene derivatives respectively, which are used as PAF-antagonists.

SUMMARY OF THE INVENTION

The present invention relates to a novel class of compounds represented by the formula

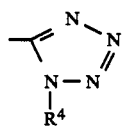

or a pharmaceutically acceptable acid addition salt thereof; wherein
one of W, X, Y, and Z is —N— and the others of W, X, Y, and Z are each —CH—;
A is
(a) a

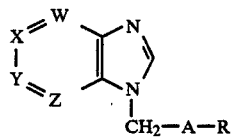

group wherein m is either 0 or 1; or
(b) a —$(CH_2)_n$—$(CR^5R^6)_p$— group wherein n is an integer from 0 to 8, p is an integer from 0 to 2, and $R^5$ and $R^6$ are independently hydrogen or $C_1$-$C_4$ alkyl; and
R is
(a) a

group wherein $R^1$ is $C_1$-$C_8$ alkyl;
(b) a

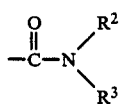

group wherein $R^2$ and $R^3$ are independently hydrogen, $C_1$-$C_8$ alkyl, or $C_3$-$C_8$ cycloalkyl;

(c) a

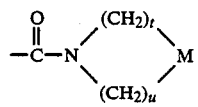

group wherein t and u are independently integers from 1 to 3 and M is —O—, —S—, or —$CH_2$—; or
(d) a

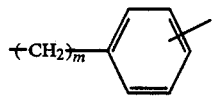

group wherein $R^4$ is hydrogen, $C_1$-$C_8$ alkyl or $C_3$-$C_8$ cycloalkyl.

The invention further relates to pharmaceutical compositions comprising a compound of formula (I). Such compounds and compositions have potent and specific PAF antagonistic activities and are thereby useful in the treatment of various diseases or disorders mediated by the PAF, for example, inflammation, cardiovascular disorders, asthma, lung edema, and adult respiratory distress syndrome.

DETAILED DESCRIPTION

As used herein the term "$C_1$-$C_8$ alkyl" refers to straight chain or branched chain hydrocarbon groups having from one to eight carbon atoms. Illustrative of such alkyl groups are methyl, ethyl, propyl, isopropyl, butyl, isobutyl, sec-butyl, tert-butyl, pentyl, neopentyl, hexyl, isohexyl, octyl and the like.

As used herein the term "$C_3$-$C_8$ cycloalkyl" includes cycloalkyl groups having from three to eight carbons. Illustrative of such cycloalkyl groups are cyclopropyl, cyclobutyl, cyclopentyl, cyclohexyl, cycloheptyl, cyclooctyl and the like.

The term "pharmaceutically acceptable acid addition salt" refers to a salt prepared by contacting a compound of formula (I) with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts.

The preferred compounds of the present invention include compounds of the formula

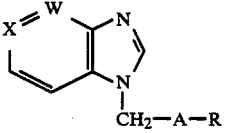

wherein one of W and X is —N— and the other of W and X is —CH—, and R is as above defined.

The compounds of formula (I), may be prepared in accordance with the following procedures:

Imidazo[4,5-b]pyridine, represented as a tautomeric mixture of the formula

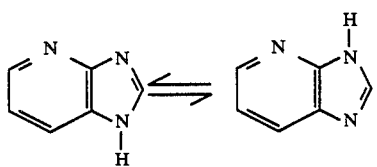

or imidazo[4,5-c]pyridine, represented as a tautomeric mixture of the formula

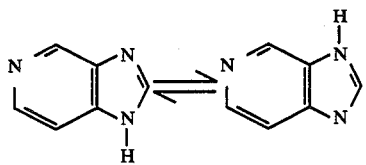

is treated with a compound of the formula

D-CH$_2$-A-R                (IV)

wherein A and R are above defined and D is chloro, bromo, iodo, methanesulfonyloxy or p-toluenesulfonyloxy. The reaction is preferrably conducted in the presence of a base, preferably sodium or potassium hydride, and an aprotic solvent, preferably dimethylformamide, to yield an isomeric mixture which is separated to yield the compounds of formula (I).

In another procedure for preparing compounds of formula (I), a substituted nitropyridine of the formula

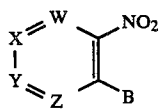

wherein W, X, Y, and Z are as above defined and B is halo or C$_1$-C$_4$ alkoxy; is treated with a substituted amino of the formula

H$_2$N-CH$_2$-A-R                (VI)

wherein A and R are as above defined to yield a substituted amino nitropyridine of the formula

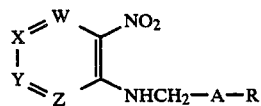

The substituted amino nitropyridine of formula (VII) is reduced, for example in the presence of hydrogen and a catalyst such as palladium or platinum, to yield a substituted diaminopyridine of the formula

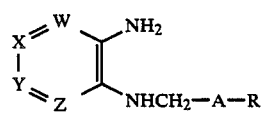

The substituted diaminopyridine of formula (VIII) is treated with dimethylformamide and triethyl orthoformate in the presence of a catalytic amount of concentrated hydrochloric acid at room temperature to yield the compounds of formula (I).

Alternatively the substituted diaminopyridines of formula (VIII) may be prepared by treating a substituted pyridine of formula (IX) with a substituted aldehyde of the formula (X).

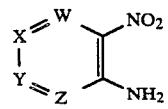

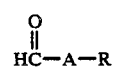

wherein A and R are as above defined; to yield an imino nitropyridine of the formula

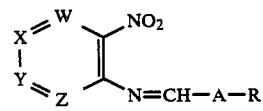

and then reducing the imino nitropyridine, for example in the presence of hydrogen and a catalyst such as palladium or platinum.

The appropriate solvents employed in the above reactions are solvents wherein the reactants are soluble but do not react with the reactants. The preferred solvents vary from reaction to reaction and are readily ascertained by one of ordinary skill in the art.

This invention also relates to a method of treatment of patients (or mammalian animals raised in the dairy, meat, or fur industries or as pets) suffering from disorders or diseases which can be attributed to PAF as previously described, and more specifically, a method of treatment involving the administration of compound (I) as the active ingredient.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by PAF, compound (I) may be administered orally, topically, parenterally, or by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients. The compounds and composition may for example be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from about 1 to 250 mg preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight.

The dosage regimen for treating an infectious disease condition with the compounds and/or compositions of this invention is selected in accordance with a variety of factors, including the type, age, weight, sex and medical condition of the patient; the severity of the infection; the route of administration; and the particular compound employed and thus may vary widely.

For therapeutic purposes, the compounds of this invention are ordinarily combined with one or more adjuvants appropriate to the indicated route of administration. If per os, the compounds may be admixed with lactose, sucrose, starch powder, cellulose esters of alkanoic acids, cellulose alkyl esters, talk, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Appropriate dosages, in any given instance, of course depend upon the nature and severity of the condition treated, the route of administration, and the species of mammal involved, including its size and any individual idiosyncrasies.

Representative carriers, diluents and adjuvants include for example, water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

Dosage levels of the order from about 1 mg to about 100 mg per kilogram of body weight per day are useful in the treatment of the above-indicated conditions (from about 50 mg to about 5 mgs. per patient per day). For example, inflammation is effectively treated and antipyretic and analgesic activity manifested by the administration from about 25 to about 75 mg of the compound per kilogram of body weight per day (about 75 mg to about 3.75 gm per patient per day). Preferably, from about 5 mg to about 50 mg per kilogram of body weight per daily dosage produces highly effective results (about 250 mg to about 2.5 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 95 mg of active agent compounded with an appropriate and convenient amount of carrier materials which may vary from about 5 to 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to further illustrate the present invention and not to limit the invention in spirit or scope. In the Examples, all parts are parts by weight unless otherwise expressly set forth.

EXAMPLE 1

(A) Ethyl 4-(3H-imidazo[4,5-c]pyridin-3-ylmethyl)benzoate and (B) Ethyl 4-(1H-imidazo[4,5-c]pyridin-1-ylmethyl)benzoate (a) Imidazo[4,5-c]pyridine A stirred mixture of 3,4-diaminopyridine (10.0 g, 0.092 mol) and formic acid (20 ml) was heated under reflux for 2.5 hours. The resulting mixture was cooled and the formic acid was evaporated off under reduced pressure to a yield a residue. The residue was dissolved in ethanol (300 ml) at 80° C. and the resulting solution was treated with calcuim carbonate (10 g) and neutralized by stirring under reflux for 1 hour. The hot mixture was filtered and the residue was washed with hot ethanol (3×300 ml). The filtrate and washings were combined and the ethanol was evaporated off under reduced pressure to yield 3,4-diformylaminopyridine as a colorless solid. The 3,4-diformylaminopyridine was heated at 200°–220° C. and 0.5 mm.Hg pressure in a Kugelrohr bulb-to-bulb distillation apparatus to yield a crude product as a distillate which solidified on cooling. The crude product was recrystallized from ethyl acetate to yield imidazo[4,5-c]pyridine as a colorless crystalline solid, having a melting point of 174°–176° C. and the following physical characteristics:

$^1$H-NMR (δ-DMSO-d$^6$): 6.60 (broad s, 1H), 7.66 (dd, 1H), 8.37 (d, 1H), 8.44 (s, 1H) and 9.00 (d, 1H).

(b) Ethyl 4-(3H-imidazo[4,5-c]pyridin-3-ylmethyl)benzoate and

Ethyl 4-(1H-imidazo[4,5-c]pyridin-1-ylmethyl)benzoate

A stirred solution of imidazo[4,5-c]pyridine (10.0 g, 0.084 mol) in dry dimethylformamide (100 ml) at 18° C. under a nitrogen atmosphere, was treated with sodium hydride (5.04 g of 60% dispersion in mineral oil, 0.126 mol) in portions over a period of 5 minutes. The mixture was stirred for an additional 2.5 hours until hydrogen evolution had ceased. The mixture was cooled to 0° C., treated with ethyl 4-bromomethylbenzoate (22.6 g, 0.093 mol), allowed to warm up to room temperature and stirred for an additional 18 hours. The mixture was diluted with ethyl acetate (600 ml), washed with water (3×200 ml) and dried over anhydrous sodium sulphate. The solvent was evaporated off under reduced pressure to yield an impure mixture of isomers which was purified by chromatography (silica gel, chloroform) to yield a less polar isomer which was recrystallized from ethyl acetate-hexane to yield ethyl 4-(3H-imidazo[4,5-c]pyridin-3-ylmethyl)benzoate as a colorless crystalline solid, having a melting point of 110°-111.5° C. and the following physical characteristics:

Elemental Analysis: C, 67.82%; H, 5.38%; N, 14.75%; as against calculated values of C, 67.88%; H, 5.41%; H, 14.84% for $C_{16}H_{15}N_3O_2.0.1H_2O$.

$^1$H-NMR ($\delta$-CDCl$_3$): 1.39 (t, 3H), 4.38 (q, 2H), 5.52 (s, 2H), 7.29 and 8.06 (ABq, 4H), 7.76 (dd, 1H), 8.11 (s, 1H), 8.48 (dd, 1H) and 8.70 (s, 1H) and represented by the structural formula:

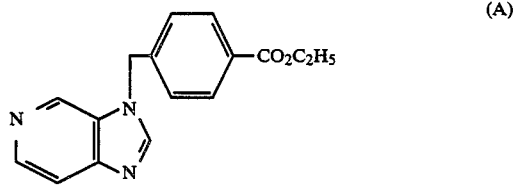

and a more polar isomer which was recrystallized from ethyl acetate-hexane to yield ethyl 4-(1H-imidazo[4,5-c]pyridin-1-ylmethyl)benzoate as a colorless crystalline solid, having a melting point of 156°-157° C. and the following physical characteristics:

Elemental Analysis: C, 68.15%; H, 5.33%; N 14.87%; as against calculated values of C, 68.31%; H, 5.37%; N, 14.94% for $C_{16}H_{15}N_3O_2$.

$^1$H-NMR ($\delta$-CDCl$_3$): 1.39 (t, 3H), 4.39 (q, 2H), 5.46 (s, 2H), 7.11 (dd, 1H), 7.27 and 8.06 (ABq, 4H), 8.04 (s, 1H), 8.42 (d, 1H) and 9.17 (s, 1H) and represented by the structural formula:

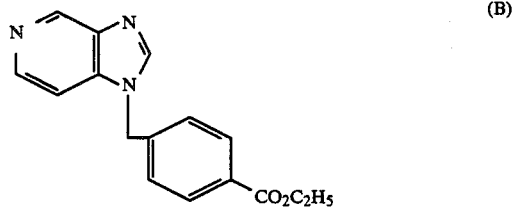

EXAMPLE 2

(A) Ethyl 3-(3H-imidazo[4,5-c]pyridin-3-ylmethyl)benzoate and (B) Ethyl 3-(1H-imidazo[4,5-c]pyridin-1-ylmethyl)benzoate Utilizing the procedure described in Example 1(b) but employing ethyl 3-bromomethylbenzoate in lieu of ethyl 4-bromomethylbenzoate yielded an impure mixture of isomers. The mixture was purified by column chromatography (silica gel, 20% hexane in chloroform) to yield a less polar isomer which was recrystallized from ethyl acetate-hexane to yield ethyl 3-(3H-imidazo[4,5-c]pyridin-3-ylmethyl)benzoate as a colorless crystalline solid, having a melting point of 102°-104° C. and the following physical characteristics:

Elemental Analysis: C, 68.22%, H, 5.33%, N, 14.81%; as against calculated values of C, 68.31%; H, 5.37%; N, 14.94% for $C_{16}H_{15}N_3O_2$.

$^1$H-NMR ($\delta$-CDCl$_3$): 1.39 (t, 3H), 4.38 (q, 2H), 5.51 (s, 2H), 7.37 (d, 1H), 7.46 (t, 1H), 7.75 (d, 1H), 8.01 (s, 1H), 8.05 (d, 1H), 8.11 (s, 11H), 8.48 (d, 1H) and 8.73 (s, 1H) and represented by the structural formula:

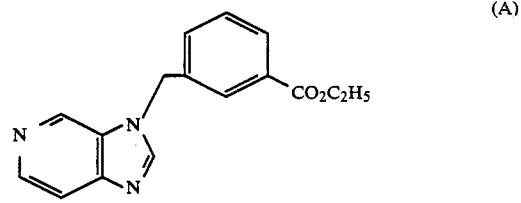

and a more polar isomer which was recrystallized from ethyl acetate-hexane to yield ethyl 3-(1H-imidazo[4,5-c]pyridin-1-ylmethyl)benzoate as a colorless crystalline solid, having a melting point of 119°-120° C. and the following physical characteristics:

Elemental Analysis: C, 67.87%; H, 5.31%, N, 14.7%; as against calculated values of C, 67.88%; H, 5.41%, N, 14.84% for $C_{16}H_{15}N_3O_2.0.1H_2O$.

$^1$H-NMR ($\delta$-CDCl$_3$): 1.39 (t, 3H), 4.39 (q, 2H), 5.45 (s, 2H), 7.24 (d, 1H), 7.32 (t, 1H), 7.45 (d, 1H), 7.88 (s, 1H), 8.04 (d, 1H), 8.06 (s, 1H), 8.42 (d, 1H) and 9.16 (s, 1H) and represented by the structural formula:

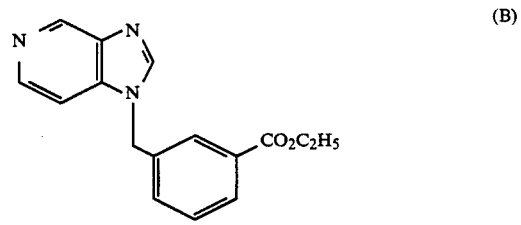

EXAMPLE 3

[4-(1H-imidazo[4,5-c]pyridin-1-ylmethyl)phenyl](4-morpholinyl)methanone

A suspension of ethyl 4-(1H-imidazo[4,5-c]pyridin-1-ylmethyl)benzoate (0.50 g, 0.0018 mol) in morpholine (10 ml) was maintained at 150° C. in a bomb calorimeter for 3 days. The morpholine was evaporated off under reduced pressure to yield a crude product which was purified by column chromatography (silica gel, 10% ethanol in chloroform) and recrystallized from diethyl ether-ethyl acetate to yield [4-(1H-imidazo[4,5-c]pyridin-1-ylmethyl)phenyl](4-morpholinyl)methanone as a colorless crystalline solid, having a melting point of 188°-190° C. and the following physical characteristics:

Elemental Analysis: C, 66.36%, H, 5.48%, N, 16.99%; as against calculated values of C, 66.32%, H, 5.69%; N, 17.19% for $C_{18}H_{18}N_4O_2.0.2H_2O$.

$^1$H-NMR ($\delta$-CDCl$_3$): 3.25-3.95 (m, 8H), 5.42 (s, 2H), 7.23 and 7.42 (ABq, 4H), 7.24 (d, 1H), 8.03 (s, 1H), 8.43

(d, 1H) and 9.17 (s, 1H) and represented by the structural formula:

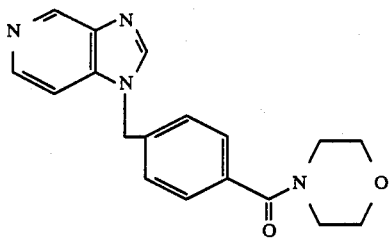

EXAMPLE 4

[4-(3H-imidazo[4,5-c]pyridin-3-ylmethyl)phenyl](4-morpholinyl)methanone

Utilizing the procedure described in Example 3 employing ethyl 4-(3H-imidazo[4,5-c]pyridin-3-ylmethyl)-benzoate in lieu of ethyl 4-(1H-imidazo[4,5-c]pyridin-1-ylmethyl)benzoate yielded a crude product which was purified by column chromatography (silica gel, chloroform) and recrystallized from diethyl ether-ethyl acetate to yield [4-(3H-imidazo[4,5-c]pyridin-3-ylmethyl)-phenyl](4-morpholinyl)methanone as a colorless crystalline solid, having a melting point of 143°–144° C. and the following physical characteristics:

Elemental Analysis: C, 67.48%, H, 5.67%, N, 17.49%; as against calculated values of C, 67.07%; H, 5.63%; N, 17.38% for $C_{18}H_{18}N_4O_2$.

$^1$H-NMR ($\delta$-CDCl$_3$): 3.35–3.95 (m, 8H), 5.50 (s, 2H), 7.28 and 7.43 (Abq, 4H), 7.77 (d, 1H), 8.12 (s, 1H), 8.49 (d, 1H) and 8.75 (s, 1H) and represented by the structural formula:

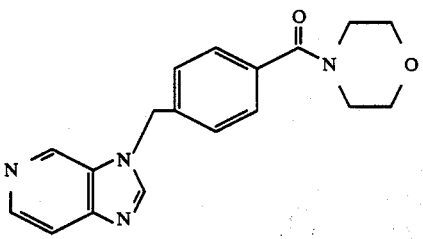

EXAMPLE 5

N-Cyclohexyl-N-methyl-4-(1H-imidazo[4,5-c]pyridin-1-yl-methyl)benzamide (a) 4-(1H-Imidazo[4,5-c]pyridin-1-ylmethyl)benzoic acid A stirred solution of ethyl 4-(1H-imidazo[4,5-c]pyridin-ylmethyl)benzoate (1.50 g, 0.0053 mol) in ethanol (5 ml) was treated with an aqueous solution of potassium hydroxide (5.5 ml of 1.0M, 0.0055 mol) and heated under reflux for 2 hours. The solvent was then evaporated off under reduced pressure to give a solid residue. The residue was triturated with toluene (100 ml) and then the toluene was evaporated off under reduced pressure to yield 4-(1H-imidazo[4,5-c]pyridin-1-ylmethyl)benzoic acid, potassium salt.

(b) N-Cyclohexyl-N-methyl-4-(1H-imidazo[4,5-c]pyridin-1-yl-methyl)benzamide

A stirred suspension of 4-(1H-imidazo[4,5-c]pyridin-1-ylmethyl)benzoic acid, potassium salt (0.78 g, 0.0027 mol) in dry dimethylformamide (5 ml) was treated with N-methylcyclohexylamine (0.36 g, 0.0032 mol) and triethylamine (0.54 g, 0.0054 mol). The reaction mixture was cooled to −5° C. and then treated with diphenylphosphoryl azide (0.81 g, 0.0030 mol). The resulting mixture was allowed to warm up to room temperature and stirred for an additional 15 hours. The solvent was evaporated off under reduced pressure to yield a crude product which was purified by column chromatography (silica gel, 5% ethanol in chloroform) and recrystallized from ethyl acetate to yield N-cyclohexyl-N-methyl-4-(1H-imidazo[4,5-c]pyridin-1-yl-methyl)benzamide as a colorless crystalline solid, having a melting point of 132°–134° C. and the following physical characteristics:

Elemental Analysis: C, 71.39%; H, 7.14%, N, 15.85%; as against calculated values of C, 71.28%; H, 7.01%; N, 15.83% for $C_{21}H_{24}N_4O.0.3H_2O$.

$^1$H-NMR ($\delta$-CDCl$_3$): 0.90–1.16 (m, 2H), 1.20–1.87 (m, 8H), 2.70–3.00 (m, 3H), 3.28–3.42 (m, 0.5H), 4.38–4.60 (m, 0.5H), 5.43 (s, 2H), 7.16–7.43 (m, 5H), 8.05 (s, 1H), 8.42 (d, 1H) and 9.17 (s, 1H) and represented by the structural formula:

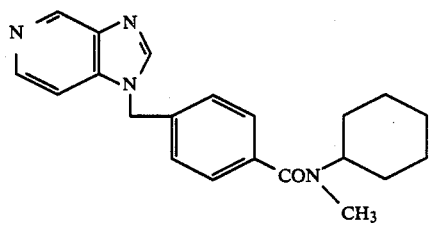

EXAMPLE 6

(A) Ethyl 4-(3H-imidazo[4,5-c]pyridin-3-yl)butanoate and (B) Ethyl 4-(1H-imidazo[4,5-c]pyridin-1-yl)butanoate Utilizing the procedure described in Example 1(b) but employing ethyl 4-bromobutyrate in lieu of ethyl 4-bromomethylbenzoate yielded an impure mixture of isomers. The mixture was purified by column chromatography (silica gel, 20% hexane in chloroform) to yield a less polar isomer ethyl 4-(3H-imidazo[4,5-b]pyridin-3-yl)butanoate as a pale-yellow oil having the following physical characteristics:

$^1$H-NMR ($\alpha$-CDCl$_3$): 1.26 (t, 3H), 2.20–2.43 (m, 4H), 4.15 (q, 2H), 4.39 (t, 2H), 7.74 (d, 1H), 8.04 (s, 1H), 8.49 (d, 1H) and 8.92 (s, 1H) and represented by the structural formula:

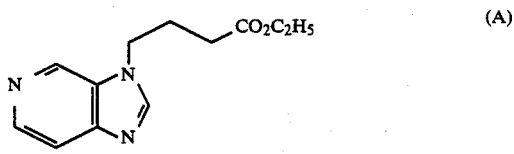

and a more polar isomer, ethyl 4-(1H-imidazo[4,5-c]pyridin-1-yl)butanoate as a pale yellow waxy solid having the following physical characteristics:

Elemental Analysis: C, 61.21%; H, 6.50%, N, 18.00%; as against calculated values of C, 61.31%, H, 6.52%, N, 17.88% for $C_{12}H_{15}N_3O_2.0.1H_2O$.

$^1$-NMR ($\delta$-CDCl$_3$): 1.26 (t, 3H), 2.24 (m, 2H), 2.36 (t, 2H), 4.14 (q, 2H), 4.31 (t, 2H), 7.41 (dd, 1H), 7.98 (s, 1H), 8.47 (d, 1H) and 9.14 (dd, 1H) and represented by the structural formula:

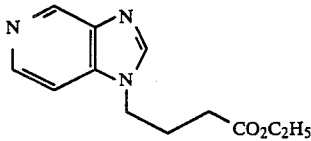
(B)

EXAMPLE 7

(A) Ethyl 5-(3H-imidazo[4,5-c]pyridin-3-yl)pentanoate
and (B) Ethyl 5-(1H-imidazo[4,5-c]pyridin-1-yl)pentanoate Utilizing the procedure described in Example 1(b) employing ethyl 5-bromopentanoate in lieu of ethyl 4-bromomethylbenzoate yielded an impure mixture of isomers. The mixture was purified by column chromatography (silica gel, 30% hexane in chloroform to 100% chloroform) to give a less polar isomer which was recrystallized from ethyl acetate-hexane to yield ethyl 5-(3H-imidazo[5,4-c]pyridin-3-yl)pentanoate as a colorless crystalline solid, having a melting point of 45°–47° C. and the following physical characteristics:

Elemental Analysis: C, 63.12%; H, 6.94%; N, 16.87%; as against calculated values of C, 63.14%; H, 6.93%; N, 16.99% for $C_{13}H_{17}N_3O_2$.

$^1$H-NMR ($\delta$-CDCl$_3$): 1.22 (t, 3H), 1.59–1.82 (m, 2H), 1.94–2.08 (m, 2H), 2.36 (t, 2H), 4.12 (q, 2H), 4.32 (t, 2H), 7.74 (d, 1H), 8.02 (s, 1H), 8.48 (d, 1H), and 8.89 (s, 1H) and represented by the structural formula:

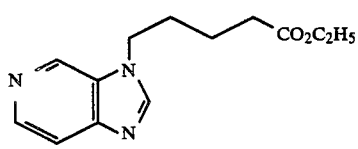
(A)

and a more polar isomer ethyl 5-(1H-imidazo[4,5-c]pyridin-1-yl)pentanoate as a pale-yellow waxy solid having the following characteristics:

Elemental Analysis: C, 61.34%; H, 6.82%; N, 16.29%; as against calculated values of C, 61.35%; H, 7.05%; N, 16.51% for $C_{13}H_{17}N_3O_2.0.4H_2O$.

$^1$H-NMR ($\delta$-CDCl$_3$): 1.24 (t, 3H), 1.60–1.76 (m, 2H), 1.88–2.00 (m, 2H), 2.37 (t, 2H), 4.12 (q, 2H), 4.23 (t, 2H), 7.37 (d, 1H), 7.99 (s, 1H), 8.46 (d, 1H) and 9.14 (s, 1H) and represented by the structural formula:

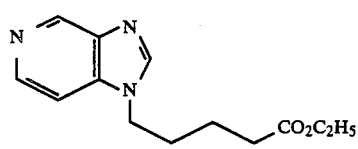
(B)

EXAMPLE 8

(A) Ethyl 6-(3H-imidazo[4,5-c]pyridin-3-yl)hexanoate
and (B) Ethyl 6-(1H-imidazo[4,5-c]pyridin-1-yl)hexanoate Utilizing the procedure described in Example 1(b) employing ethyl 6-bromohexanoate in lieu of ethyl 4-bromomethylbenzoate yielded an impure mixture of isomers. The mixture was purified by column chromatography (silica gel, chloroform) to yield a less polar isomer ethyl 6-(3H-imidazo[4,5-c]pyridin-3-yl)hexanoate as a pale yellow oil, having the following physical characteristics:

Elemental Analysis: C, 64.31%; H, 7.46%; N, 15.89%; as against calculated values of C, 64.35%; H, 7.33%; N, 16.08% for $C_{14}H_{19}N_3O_2$.

$^1$H-NMR ($\delta$-CDCl$_3$): 1.25 (t, 3H), 1.30–1.50 (m, 2H), 1.62–1.80 (m, 2H), 1.90–2.08 (m, 2H), 2.30 (t, 2H), 4.12 (q, 2H), 4.30 (t, 2H), 7.74 (d, 1H), 8.03 (s, 1H), 8.49 (d, 1H) and 8.89 (s, 1H) and represented by the structural formula:

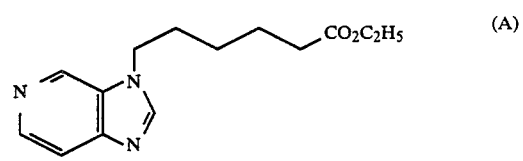
(A)

and a more polar isomer ethyl 6-(1H-imidazo[4,5-c]pyridin-1-yl)hexanoate as a pale yellow oil, having the following physical characteristics:

Elemental Analysis: C, 63.82%; H, 7.45%; N, 16.22%; as against calculated values of C, 63.91%; H, 7.35%; N, 15.97% for $C_{14}H_{19}N_3O_2.0.1H_2O$.

$^1$H-NMR ($\delta$-CDCl$_3$): 1.24 (t, 3H), 1.30–1.46 (m, 2H), 1.61–1.78 (m, 2H), 1.84–2.00 (m, 2H), 2.31 (t, 2H), 4.13 (q, 2H), 4.23 (t, 2H), 7.36 (d, 1H), 7.98 (s, 1H), 8.46 (d, 1H), and 9.13 (s, 1H) and represented by the structural formula:

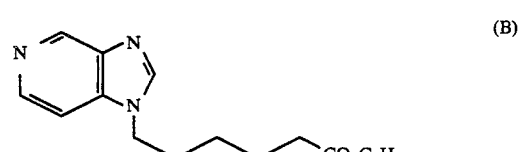
(B)

EXAMPLE 9

(A) Ethyl 7-(3H-imidazo[4,5-c]pyridin-3-yl)heptanoate
and (B) Ethyl 7-(1H-imidazo[4,5-c]pyridin-1-yl)heptanoate Utilizing the procedure described in Example 1(b) employing ethyl 7-bromoheptanoate in lieu of ethyl 4-bromomethylbenzoate yielded an impure mixture of isomers. The mixture was purified by column chromatography (silica gel, 10% hexane in chloroform) to yield a less polar isomer which was recrystallized from ethyl acetate-hexane to yield ethyl 7-(3H-imidazo[4,5-c]pyridin-3-yl)heptanoate as a colorless crystalline solid, having a melting point of 64°–65° C. and the following physical characteristics:

Elemental Analysis: C, 65.61%; H, 7.55%; N, 14.94%; as against calculated values of C, 65.43%; H, 7.69%; N, 15.26% for $C_{15}H_{21}N_3O_2$.

$^1$H-NMR ($\delta$-CDCl$_3$): 1.26 (t, 3H), 1.34–1.49 (m, 4H), 1.55–1.71 (m, 2H), 1.89–2.08 (m, 2H), 2.30 (t, 2H), 4.13 (q, 2H), 4.29 (t, 2H), 7.73 (dd, 1H), 8.02 (s, 1H), 8.48 (d, 1H) and 8.89 (d, 1H) and represented by the structural formula:

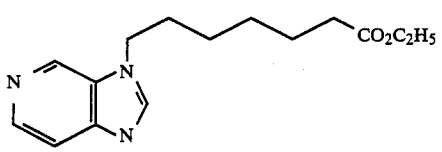

(A)

and a more polar isomer ethyl 7-(1H-imidazo[4,5-c]pyridin-1-yl)heptanoate as a pale-yellow oil, having the following physical characteristics:

Elemental Analysis: C, 65.27%; H, 7.58%; N, 14.83%; as against calculated values of C, 65.43%; H, 7.69%; N, 15.26% for $C_{15}H_{21}N_3O_2$.

$^1$H-NMR ($\delta$-CDCl$_3$): 1.24 (t, 3H), 1.28–1.48 (m, 4H), 1.54–1.72 (m, 2H), 1.84–2.00 (m, 2H), 2.29 (t, 2H), 4.12 (q, 2H), 4.20 (t, 2H), 7.37 (dd, 1H), 7.98 (s, 1H), 8.46 (d, 1H) and 9.13 (d, 1H) and represented by the structural formula:

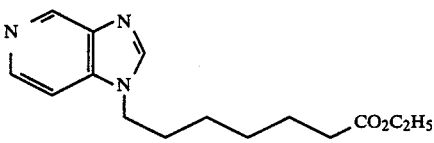

(B)

EXAMPLE 10

(A) Ethyl 2,2-dimethyl-6-(3H-imidazo[4,5-c]pyridin-3-yl)hexanoate and (B) Ethyl 2,2-dimethyl-6-(1H-imidazo[4,5-c]pyridin-1-yl)hexanoate (a) Ethyl 2,2-dimethyl-6-bromohexanoate A solution of n-butyllithium (1.6M, 63 ml, 0.10 mol) in hexane was added dropwise to a solution of diisopropylamine (10.1 g, 0.10 mol) in anhydrous tetrahydrofuran (100 ml) at −50° C. The mixture was stirred for 0.5 hours. The mixture was cooled to −70° C. and a solution of ethyl isobutyrate (12.2 g, 0.105 mol) in tetrahydrofuran (20 ml) was added. The resulting mixture was stirred at −70° C. for 1 hour. 1,4-Dibromobutane (30.4 g, 0.14 mol) was added to the mixture followed by hexamethylphosphoramide (30 g). The resulting mixture was maintained at −70° C. for 0.5 hours and then warmed to room temperature over 1 hour. The solvent was evaporated off under reduced pressure and the residue was treated with saturated aqueous ammonium chloride (500 ml) and extracted with ethyl acetate (2×150 ml). The combined extracts were washed with water (100 ml), hydrochloric acid (1N, 2×100 ml) was saturated aqueous sodium hydrogen carbonate (100 ml) and dried over anhydrous magnesium sulfate. The solvent was evaporated off under reduced pressure and the residue was distilled to yield ethyl 2,2-dimethyl-6-bromohexanoate as a pale yellow oil, having a boiling point of 73° C., 0.06 mm.Hg and the following physical characteristics:

$^1$H-NMR ($\delta$-CDCl$_3$): 1.20 (s, 6H), 1.28 (t, 3H), 1.35–1.62 (m, 4H), 1.78–2.00 (quintet, 2H), 3.42 (t, 2H) and 4.15 (q, 2H).

(b) Ethyl 2,2-dimethyl-6-(3H-imidazo[4,5-c]pyridin-3-yl)-hexanoate and Ethyl 2,2-dimethyl-6-(1H-imidazo[4,5-c]pyridin-1-yl)hexanoate Utilizing the procedure described in Example 1(b) employing ethyl 2,2-dimethyl-6-bromohexanoate in lieu of ethyl 4-bromomethylbenzoate yielded an impure mixture of isomers. The mixture was purified by column chromatography (silica gel, 15% hexane in chloroform) to yield a less polar isomer, ethyl 2,2-dimethyl-6-(3H-imidazo[4,5-c]pyridin-3-yl)hexanoate as a pale-yellow oil having the following physical characteristics:

Elemental Analysis: C, 65.17%; H, 8.01%; N, 13.83%; as against calculated values of C, 64.80%; H, 8.09%; N, 14.17% for $C_{16}H_{23}N_3O_2.0.4H_2O$.

$^1$H-NMR ($\delta$-CDCl$_3$): 1.15 (s, 6H), 1.19 (t, 3H), 1.20–1.40 (m, 2H), 1.52–1.65 (m, 2H), 1.86–2.00 (m, 2H), 4.11 (q, 2H), 4.28 (t, 2H), 7.73 (d, 1H), 8.02 (s, 1H), 8.49 (d, 1H) and 8.88 (s, 1H) and represented by the structural formula:

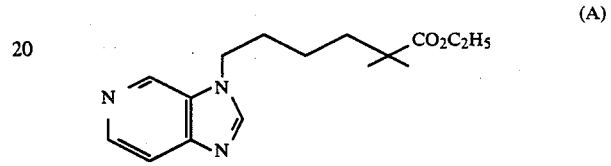

(A)

and a more polar isomer ethyl 2,2-dimethyl-6-(1H-imidazo[4,5-c]pyridin-1-yl)hexanoate as a pale-yellow oil, having the following physical characteristics:

Elemental Analysis: C, 65.12%; H, 7.86%; N, 14.87%; as against calculated values of C, 65.59%; H, 8.05%; N, 14.34% for $C_{16}H_{23}N_3O_2.0.2H_2O$.

$^1$H-NMR ($\delta$-CDCl$_3$): 1.15 (s, 6H), 1.20 (t, 3H), 1.18–1.38 (m, 2H), 1.52–1.64 (m, 2H), 1.82–1.98 (m, 2H), 4.09 (q, 2H), 4.20 (t, 2H), 7.35 (dd, 1H), 7.96 (s, 1H), 8.46 (d, 1H) and 9.15 (d, 1H) and represented by the structural formula:

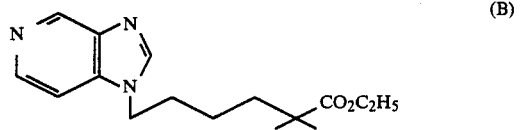

(B)

EXAMPLE 11

(A) N-Cyclohexyl-N-Methyl-7-(3H-imidazo[4,5-c]pyridin-3-yl)heptanamide and (B) N-Cyclohexyl-N-methyl-7-(1H-imidazo[4,5-c]-pyridin-1-yl heptanamide (a) 7-(3H-Imidazo[4,5-c]pyridin-3-yl)heptanoic acid and 7-(1H-Imidazo[4,5-c]pyridin-3-yl)heptanoic acid Utilizing the procedure described in Example 5(a) employing a mixture of ethyl 7-(3H-imidazo[4,5-c]pyridin-3-yl)heptanoate and ethyl 7-(1H-imidazo[4,5-c]pyridin-1-yl)heptanoate in lieu of ethyl 4-(1H-imidazo[4,5-c]pyridin-1-ylmethyl)benzoate yielded a mixture of 7-(3H-imidazo[4,5-c]pyridin-3-yl)heptanoic acid and 7-(1H-imidazo[4,5-c]pyridin-1-yl)heptanoic acid, potassium salt.

(b) N-Cyclohexyl-N-methyl-7-(3H-imidazo[4,5-c]pyridin-3-yl)heptanamide and N-Cyclohexyl-N-methyl-7-(1H-imidazo[4,5-c]pyridin-1-yl)heptanamide Utilizing the procedure described in Example 5(b) employing a mixture of 7-(3H-imidazo[4,5-c]pyridin-3- yl)heptanoic acid and 7-(1H-imidazo[4,5-c]pyridin-1-yl)heptanoic acid, potassium salts in lieu of 4-(1H-imidazo[4,5-c]pyridin-1-ylmethyl) benzoic acid, potassium salt yielded an impure mixture of isomers. The mixture was purified by column chromatography (silica gel, 5% ethanol in chloroform) to yield a less polar isomer N-cyclohexyl-N-methyl-7-(3H-imidazo[4,5-c]pyridin-3-yl)heptanamide as a pale-yellow oil, having the following physical characteristics:

Elemental Analysis: C, 70.41%; H, 8.75%; N, 16.49%; as against calculated values of C, 70.14%; H, 8.83%; N, 16.36% for $C_{20}H_{30}N_4O$.

$^1$H-NMR ($\delta$-CDCl$_3$): 0.98–2.08 (m, 17.5H), 2.18–2.37 (m, 2H), 2.47–2.65 (m, 0.5H), 2.81 (s, 3H), 3.41–3.58 (m, 0.5H), 4.29 (t, 2H), 4.31–4.54 (m, 0.5H), 7.73 (d, 1H), 8.04 (s, 1H), 8.48 (d, 1H), and 8.90 (s, 1H) and represented by the structural formula:

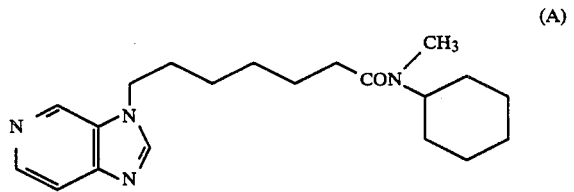

(A)

and a more polar isomer N-cyclohexyl-N-methyl-7-(1H-imidazo[4,5-c]pyridin-1-yl)heptanamide, as a pale-yellow oil having the following physical characteristics:

$^1$H-NMR ($\delta$-CDCl$_3$): 0.98–2.08 (m, 17.5H), 2.20–2.46 (m, 2H), 2.80 (s, 3H), 3.20–3.90 (m, 1H), 4.22 (t, 2H), 4.30–4.52 (m, 0.5H), 7.41 (d, 1H), 8.01 (s, 1H), 8.46 (d, 1H) and 9.12 (s, 1H) and represented by the structural formula:

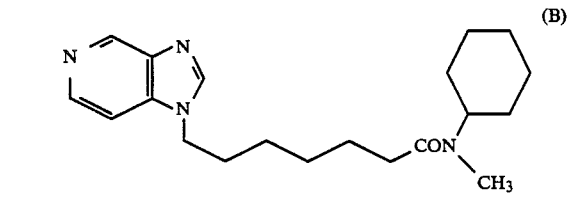

(B)

EXAMPLE 12

(A)
3-[4-(1-Cyclohexyl-1H-tetrazol-5-yl)butyl]-3H-imidazo[4,5-c]pyridine and (B)
1-[4-(1-Cyclohexyl-1H-tetrazol-5-yl)butyl]-1H-imidazo[4,5-c]pyridine (a) N-Cyclohexyl-5-chloropentanamide A stirred solution of 5-chlorovaleryl chloride (50.0 g, 0.322 mol) in dichloromethane (300 ml) at 0° C. was treated dropwise with a solution containing cyclohexylamine (31.68 g, 0.320 mol), triethylamine (32.32 g, 0.320 mol) and dimethylaminopyridine (0.02 g) in dichloromethane (300 ml). The resulting solution was stirred for 2 hours at 0° C. and then for an additional 16 hours at room temperature. The solution was diluted with dichloromethane (400 ml), washed with water (3×200 ml), saturated aqueous sodium hydrogen carbonate (3×100 ml), saturated aqueous ammonium chloride (3×100 ml), and brine (2×100 ml) and then dried over anhydrous sodium sulfate. The solvent was evaporated off under reduced pressure to yield a crude product.

The crude product was recrystallized from ethyl acetate-hexane to yield N-cyclohexyl-5-chloropentanamide as a colorless crystalline solid, having a melting point of 70°–71° C. and the following physical characteristics:

Elemental Analysis: C, 60.75%; H, 9.33%; N, 6.42%; as against calculated values of C, 60.68%; H, 9.26%; N, 6.43% for $C_{11}H_{20}ClNO$.

$^1$H-NMR ($\delta$-CDCl$_3$): 1.00–2.00 (m, 14H), 2.19 (t, 2H), 3.55 (t, 2H), 3.67–3.88 (m, 1H), 5.27–5.60 (broad s, 1H).

(b) 5-(4-Chlorobutyl)-1-cyclohexyl-1H-tetrazole

A stirred solution of N-cyclohexyl-5-chloropentanamide (4.36 g, 0.020 mol) in benzene (30 ml) at 0° C. was treated with phosphorous pentachloride (4.4 g, 0.021 mol) in portions over 10 minutes. When the addition was complete the reaction was stirred for an additional 2 hours at 18° C. The solution was then cooled to 0° C. and treated with a solution of hydrazoic acid (0.04 mol) in benzene (50 ml) (prepared according to the method described in Reagents for Organic Synthesis, Volume 1, L. F. Fieser and M. Fieser, John Wiley and Sons (New York: 1967). The resulting solution was stirred at 0° C. for an additional 1.5 hours and at 18° C. for 48 hours and then heated under reflux for an additional 3 hours. The solvent was evaporated off under reduced pressure and the resulting residue was dissolved in ethyl acetate (250 ml). The resulting solution was washed with saturated aqueous sodium hydrogen carbonate (3×100 ml), dried over anhydrous sodium sulfate, filtered, and concentrated under reduced pressure to yield a crude product. The crude product was purified by recrystallization from ethyl acetate-hexane to yield 5-(4-chlorobutyl)-1-cyclohexyl-1H-tetrazole as a colorless crystalline solid, having a melting point of 50°–51° C. and the following physical characteristics:

Elemental Analysis: C, 54.52%; H, 7.95%; N, 23.30%; as against calculated values of C, 54.43%; H, 7.89%; N, 23.08% for $C_{11}H_{19}ClN_4$.

$^1$H-NMR ($\delta$-CDCl$_3$): 1.24–2.16 (m, 14H), 2.91 (t, 2H), 3.63 (t, 2H), 4.04–4.22 (m, 1H).

(c) 3-[4-(1-Cyclohexyl-1H-tetrazol-5-yl)butyl]-3H-imidazo[4,5-pyridine and 1-[4(1-Cyclohexyl-1H-tetrazol-5-yl)butyl]1H-imidazo[4,5-c]pyridine Utilizing the procedure described in Example 1(b) employing 5-(4-chlorobutyl)-1-cyclohexyl-1H-tetrazole in lieu of ethyl 4-bromomethylbenzoate yielded a crude mixture of isomers. The mixture was purified by column chromatography (silica gel, chloroform) to yield a less polar isomer which was recrystallized from diethyl ether-chloroform to yield 3[4-(1-cyclohexyl-1H-tetrazol-5-yl)butyl]-3H-imidazo[4,5-c]pyridine as a colorless crystalline solid, having a melting point of 133°–135° C. and the following physical characteristics:

Elemental Analysis: C, 62.63%; H, 7.08%; N, 29.89%; as against calculated values of C, 62.75%; H, 7.12%; N, 30.13% for $C_{17}H_{23}N_7$.

$^1$H-NMR ($\delta$-CDCl$_3$): 1.24.2.20 (m, 14H), 2.85 (t, 2H), 3.96–4.15 (m, 1H), 4.39 (t, 2H), 7.74 (dd, 1H), 8.06 (s, 1H), 8.49 (d, 1H) and 8.90 (d, 1H) and represented by the structural formula:

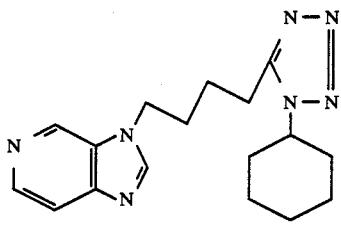

(A)

and a more polar isomer which was recrystallized from diethyl ether-chloroform to yield 1-[4-(1-cyclohexyl-1H-tetrazol-5-yl)butyl]-1H-imidazo[4,5-c]pyridine as a colorless crystalline solid, having a melting point of 93°–95° C. and the following physical characteristics:

Elemental Analysis: C, 62.60%; H, 7.10%; N, 30.00%; as against calculated values of C, 62.75%; H, 7.12%; N, 30.13% for $C_{17}H_{23}N_7$.

$^1$H-NMR (δ-CDCl$_3$): 1.20–2.24 (m, 14H), 2.85 (t, 2H), 3.92–4.10 (m, 1H), 4.30 (t, 2H), 7.38 (d, 1H), 8.00 (s, 1H), 8.46 (d, 1H) and 9.14 (s, 1H) and represented by the structural formula:

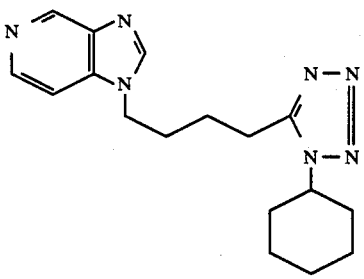

(B)

EXAMPLE 13

1-[5-(1-Cyclohexyl-1H-tetrazol-5-yl)pentyl]-1H-imidazo[4,5-c]pyridine (a) N-Cyclohexyl-6-bromohexanamide Utilizing the procedure described in Example 14(a) employing 6-bromohexanoyl chloride in lieu of 5-chlorovaleryl chloride yielded a crude product which was purified by recrystallization from dichloromethane-pentane to yield N-cyclohexyl-6-bromohexanamide as a colorless crystalline solid, having a melting point of 73°–74° C. (morphological change at 65°–68° C.) and the following physical characteristics:

Elemental Analysis: C, 52.21%; H, 7.88%; N, 4.88%; as against calculated values of C, 52.18%; H, 8.03%; N, 5.07% for $C_{12}H_{22}BrNO$.

$^1$H-NMR (δ-CDCl$_3$): 1.00–2.00 (m, 16H), 2.16 (t, 2H), 3.42 (t, 2H), 3.66–3.86 (m, 1H) and 5.36 (broad s, 1H).

(b) 5-(5-Bromopentyl)-1-cyclohexyl-1H-tetrazole

Utilizing the procedure described in Example 14(b) employing N-cyclohexyl-6-bromohexanamide in lieu of N-cyclohexyl-5-chloropentanamide yielded a crude product which was purified by crystallization from ethyl acetate-hexane to yield 5-(5-bromopentyl)-1-cylohexyl-1H-tetrazole as a colorless crystalline solid, having a melting point of 57°–59° C. and the following physical characteristics:

$^1$H-NMR (δ-CDCl$_3$): 1.30–2.14 (m, 16H), 2.85 (t, 2H), 3.43 (t, 2H) and 4.06–4.22 (m, 1H).

(c) 1-[5-(1-Cyclohexyl-1H-tetrazol-5-yl)pentyl]-1H-imidazo[4,5-c]pyridine

Utilizing the procedure described in Example 1(b) employing 5-(5-bromopentyl)-1-cyclohexyl-1H-tetrazole in lieu of ethyl 4-bromomethylbenzoate yielded an impure mixture of isomers. The mixture was purified by column chromatography (silica gel, 30% hexane in chloroform) to yield 1-[5-(1-cyclohexyl-1H-tetrazol-5-yl)pentyl]-1H-imidazo[4,5-c]pyridine as a colorless oil having the following physical characteristics:

Elemental Analysis: C, 62.28%; H, 7.45%; N, 27.65%; as against calculated values of C, 61.85%; H, 7.58%; N, 28.05% for $C_{18}H_{25}N_7.0.55H_2O$.

$^1$H-NMR (δ-CDCl$_3$): 1.28–1.56 (m, 4H), 1.43–2.12 (m, 12H), 2.80 (t, 2H), 4.00–4.14 (m, 1H), 4.25 (t, 2H), 7.37 (dd, 1H), 7.99 (s, 1H), 8.48 (d, 1H) and 9.16 (d, 1H) and represented by the structural formula:

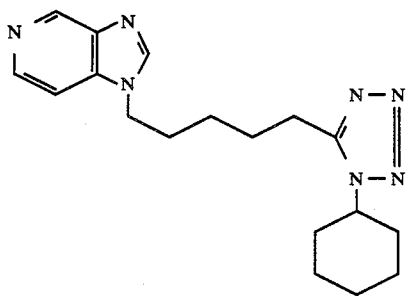

EXAMPLE 14

(A) Ethyl 4-(3H-imidazo[4,5-b]pyridin-3-ylmethyl)benzoate and (B) Ethyl 4-(1H-imidazo[4,5-b]pyridin-1-ylmethyl)benzoate Utilizing the procedures described in Example 1 employing 2,3-diaminopyridine in lieu of 3,4-diaminopyridine (and thus imidazo[4,5-b]pyridine in lieu of imidazo[4,5-c]pyridine) yielded an impure mixture of isomers. The mixture was purified by column chromatography (silica gel, chloroform) to yield a less polar isomer which was recrystallized from ethyl acetate-hexane to yield ethyl 4-(3H-imidazo[4,5-b]pyridin-3-ylmethyl)-benzoate as a colorless crystalline solid, having a melting point of 104°–106° C. and the following physical characteristics:

Elemental Analysis: C, 67.93%; H, 5.29%; N, 14.88%; as against calculated values of C, 68.31%; H, 5.37%; N, 14.94% for $C_{16}H_{15}N_3O_2$.

$^1$H-NMR (δ-CDCl$_3$): 1.36 (t, 3H), 4.37 (q, 2H), 5.56 (s, 2H), 7.28 (dd, 1H), 7.34 and 8.02 (ABq, 4H), 8.08 (s, 1H), 8.12 (dd, 1H) and 8.43 (dd, 1H) and represented by the structural formula:

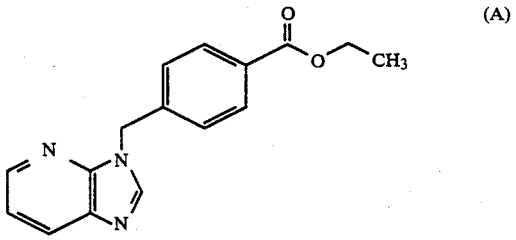

(A)

and a more polar isomer which was recrystallized from ethyl acetate-hexane to yield ethyl 4-(1H-imidazo[4,5-b]pyridin-1-ylmethyl)benzoate as a colorless crystalline solid, having a melting point of 142°-143° C. and the following physical characteristics:

Elemental Analysis: C, 68.26%; H, 5.34%; N, 14.92%; as against calculated values of C, 68.31%; H, 5.37%; N, 14.94% for $C_{16}H_{15}N_3O_2$.

$^1$H-NMR ($\delta$-CDCl$_3$): 1.38 (t, 3H), 4.37 (q, 2H), 5.46 (s, 2H), 7.19 (dd, 1H), 7.25 and 8.05 (ABq, 4H), 7.55 (s, 1H), 8.24 (dd, 1H) and 8.60 (dd, 1H) and represented by the structural formula:

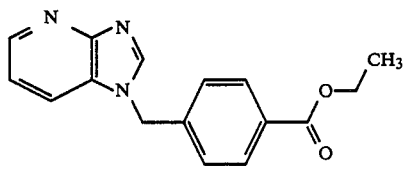

(B)

EXAMPLE 15

[4-(1H-Imidazo[4,5-b]pyridin-1-ylmethyl)phenyl](4-morpholinyl)methanone (a) 4-(1H-Imidazo[4,5-b]pyridin-1-ylmethyl)benzoic acid A stirred solution of ethyl 4-(1H-imidazo[4,5-b]pyridin-1-ylmethyl)benzoate (1.50 g, 0.0053 mol) in ethanol (5 ml) was treated with an aqueous solution of potassium hydroxide (5.5 ml of 1.0M, 0.0055 mol) and heated under reflux for 2 hours. The solvent was then evaporated off under reduced pressure to give a solid residue. The residue was triturated with toluene (100 ml) and then the toluene was evaporated off under reduced pressure to yield 4-(1H-imidazo[4,5-b]pyridin-1-ylmethyl)benzoic acid, potassium salt.

(b) [4-(1H-Imidazo[4,5-b]pyridin-1-ylmethyl)phenyl](4-morpholinyl)methanone

A stirred suspension of 4-(1H-imidazo[4,5-b]pyridin-1-ylmethyl)benzoic acid, potassium salt (0.50 g, 0.00172 mol) in dry dimethylformamide (5 ml) was treated with morpholine (0.19 g, 0.00214 mol) and triethylamine (0.36 g, 0.00356 mol). The reaction mixture was then cooled to $-5°$ C. and treated with diphenylphosphoryl azide (0.54 g, 0.00196 mol). The resulting mixture was allowed to warm up to room temperature and stirred for an additional 15 hours. The solvent and excess reagents were evaporated off under reduced pressure to yield a crude product which was purified by column chromatography (silica gel, 10% ethanol in chloroform) and recrystallized from ethyl acetate to yield [4-(1H-imidazo[4,5-c]pyridin-1-ylmethyl)phenyl](4-morpholinyl)methanone as a colorless crystalline solid, having a melting point of 119°-121° C. and the following physical characteristics:

Elemental Analysis: C, 66.64%; H, 5.52%; N, 17.40%; as against calculated values of C, 66.69%; H, 5.66%; N, 17.28% for $C_{18}H_{18}N_4O_2.0.1H_2O$.

$^1$H-NMR ($\delta$-CDCl$_3$): 3.20–4.00 (m, 8H), 5.43 (s, 2H), 7.22 (dd, 1H), 7.24 and 7.42 (ABq, 4H), 7.59 (dd, 1H), 8.22 (s, 1H) and 8.60 (dd, 1H) and represented by the structural formula:

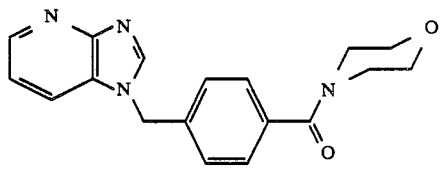

EXAMPLE 16

(A)
3-[4-(1-Cyclohexyl-1H-tetrazol-5-yl)butyl]-3H-imidazo[4,5-b]pyridine and (B)
1-[4-(1-Cyclohexyl-1H-tetrazol-5-yl)butyl]-1H-imidazo[4,5-b]pyridine Utilizing the procedure described in Example 1(a) employing 5-(4-chlorobutyl)-1-cyclohexyl-1H-tetrazole in lieu of ethyl 4-bromomethylbenzoate and imidazo[4,5-b]pyridine in lieu of imidazo[4,5-c]pyridine yielded an impure mixture of isomers. The mixture was purified by column chromatography (silica gel, 5% ethanol in chloroform) to yield a less polar isomer which was recrystallized from diethyl ether-chloroform to yield 3-[4-(1-cylohexyl-1H-tetrazol-5-yl)butyl]-3H-imidazo[4,5-b]pyridine as a colorless crystalline solid, having a melting point of 94°-95° C. and the following physical characteristics:

Elemental Analysis: C, 62.16%; H, 7.12%; N, 29.50%; as against calculated values of C, 62.06%; H, 7.17%; N, 29.80% for $C_{17}H_{23}N_7.0.2H_2O$.

$^1$H-NMR ($\delta$-CDCl$_3$): 1.24–1.50 (m, 4H), 1.60–2.20 (m, 12H), 2.89 (t, 2H), 3.99–4.14 (m, 1H), 4.40 (t, 2H), 7.27 (dd, 1H), 8.10 (s, 1H), 8.10 (dd, 1H) and 8.41 (dd) and represented by the structural formula:

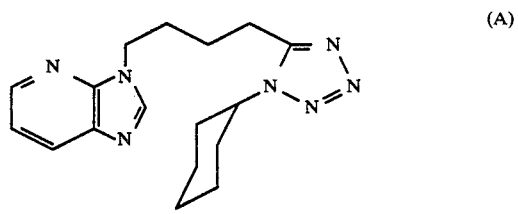

(A)

and a more polar isomer which was recrystallized from diethylether-chloroform to yield 1-[4-(1-cyclohexyl-1H-tetrazol-5-yl)butyl]-1H-imidazo[4,5-b]pyridine as a colorless crystalline solid, having a melting point of 143°-146° C. and the following physical characteristics:

Elemental Analysis: C, 62.29%; H, 7.06%; N, 29.94%; as against calculated values of C, 62.40%; H, 7.15%; N, 29.96% for $C_{17}H_{23}N_7.0.1H_2O$.

$^1$H-NMR ($\delta$-CDCl$_3$): 1.22–1.50 (m, 2H), 1.60–2.20 (m, 12H), 2.84 (t, 2H), 3.95–4.10 (m, 1H), 4.30 (t, 2H), 7.27 (dd, 1H), 7.78 (dd, 1H), 8.14 (s, 1H) and 8.61 (dd, 1H) and represented by the structural formula:

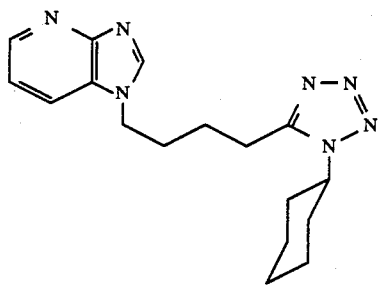
(B)

EXAMPLE 17

PAF-Induced Primary Aggregation in Human Platelet-Rich Plasma

Human venous blood was collected from healthy male donors, who had denied any medication during the previous 14 days. Nine volumes of blood were mixed with one volume of 3.24% trisodium citrate. The citrated blood was centrifuged at 160 g for ten minutes at 22° C. to obtain platelet rich plasma (PRP). The platelets were then counted on a Coulter counter, and the platelet count was adjusted to 200,000 per $\mu$l with plasma. The PRP was then treated with indomethacin dissolved in dimethylsulfoxide (10 $\mu$g indomethacin per ml PRP). A stock solution of PAF ($C_{16}$ or $C_{18}$ $\beta$-acetyl-$\gamma$-O-alkyl-L-$\alpha$-phosphatidylcholine; 1 mg/ml) was prepared as a solution in chloroform-methanol (9:1 v/v). A 10 $\mu$l portion of the stock solution was evaporated to dryness under nitrogen and dissolved in 0.15M sodium chloride-0.15M Tris.HCl (90:10 v/v) buffer containing 0.25% bovine albumin. Small volumes of the PAF solution (5–15 $\mu$l) were added to 0.5 ml samples of indomethacin-treated PRP and the aggregation trace was recorded using an aggregometer. A dose reponse curve was obtained and a sub-optimal dose of PAF was determined for use in inhibition studies.

Indomethacin-treated PRP (0.5 ml) was incubated with a test compound dissolved in buffer (ca. pH 5) or dimethylsulfoxide for two minutes at 37° C. prior to addition of the sub-optimal dose of PAF. The subsequent aggregation trace was recorded and the present inhibition of PAF primary aggregation was determined by comparison with a control PAF-induced aggregation trace. (Due to variability in PAF-induced aggregation within a given PRP sample, a control PAF-induced aggregation was determined every two or three samples.) An inhibition dose-response curve was determined for each test compound and the $IC_{50}$ value calculated. Table I lists $IC_{50}$'s for illustrative examples of the compounds of this invention.

TABLE I

PAF-induced primary aggregation in human platelet-rich plasma

| Compound, [Example number] | $IC_{50}$ ($\mu$M) |
| --- | --- |
| 1(A) | 136 |
| 1(B) | 46 |
| 2(A) | 165 |
| 2(B) | 80 |
| 3 | 49.5 |
| 4 | 215 |
| 5 | 5 |
| 6(A) | 140 |
| 7(A) | 500 |

TABLE I-continued

PAF-induced primary aggregation in human platelet-rich plasma

| Compound, [Example number] | $IC_{50}$ ($\mu$M) |
| --- | --- |
| 7(B) | 185 |
| 8(A) | 102 |
| 8(B) | 20.5 |
| 9(A) | 48 |
| 9(B) | 20 |
| 10(A) | 43.5 |
| 10(B) | 15 |
| 11(A) | 500 |
| 12(A) | 56 |
| 12(B) | 8 |
| 13 | 33 |
| 14(A) | 58 |
| 14(B) | 29 |
| 15 | 87 |
| 16(A) | 118 |
| 16(B) | 112 |

Although this invention has been described with respect to specific modification, the details thereof are not to be construed as limitations, for it will be apparent that various equivalents, changes and modifications may be restored and modification may be resorted to without departing from the spirit and scope thereof and it is understood that such equivalent embodiments are intended to be included therein.

What is claimed is:

1. A compound of the formula

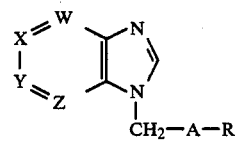

or a pharmaceutically acceptable acid addition salt thereof; wherein one of W, X, Y, and Z is —N— and the others of W, X, Y, and Z are each —CH—;
A is
(a) a

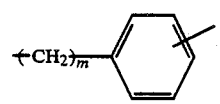

group wherein m is 0 or 1, or
(b) a —$(CH_2)_n$—$(CR^5R^6)_p$— group wherein n is an integer from 0 to 8, p is an integer from 0 to 2, and $R^5$ and $R^6$ are independently hydrogen or $C_1$-$C_4$ alkyl; and
R is
(a) a

group wherein $R^1$ is $C_1$-$C_8$ alkyl;
(b) a

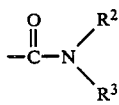

group wherein R² and R³ are independently hydrogen, C₁-C₈ alkyl, or C₃-C₈ cycloalkyl;

(c) a

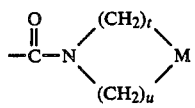

group wherein t and u are independently integers from 1 to 3 and M is —O—, —S—, or —CH₂—; or (d) a

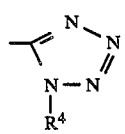

group wherein R⁴ is hydrogen, C₁-C₈ alkyl, or C₃-C₈ cycloalkyl.

2. A compound according to claim 1 having the formula

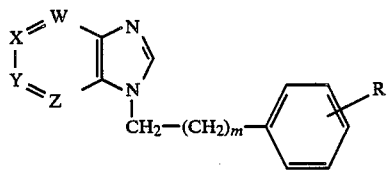

3. A compound according to claim 2 having the formula

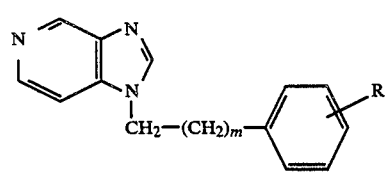

4. A compound according to claim 3 wherein R is a

group.

5. A compound according to claim 4 wherein m is 0.

6. A compound according to claim 4 wherein R¹ is ethyl.

7. A compound according to claim 4 which is ethyl 4-(1H-imidazo[4,5-c]pyridin-1-ylmethyl)benzoate.

8. A compound according to claim 4 which is ethyl 3-(1H-imidazo[4,5-c]pyridin-1-ylmethyl)benzoate.

9. A compound according to claim 3 wherein R is a

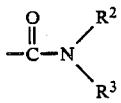

group.

10. A compound according to claim 9 wherein m is 0.

11. A compound according to claim 9 wherein R² and R³ are independently C₁-C₈ alkyl or C₃-C₈ cycloalkyl.

12. A compound according to claim 9 which is N-cyclohexyl-N-methyl-4-[1H-imidazo[4,5-c]pyridin-1-ylmethyl]benzamide.

13. A compound according to claim 3 wherein R is a

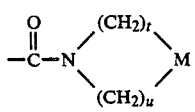

group.

14. A compound according to claim 13 wherein m is 0.

15. A compound according to claim 13 wherein M is —O—.

16. A compound according to claim 13 which is [4-(1H-imidazo[4,5-c]pyridin-1-ylmethyl)phenyl](4-morpholinyl)methanone.

17. A compound according to claim 2 having the formula

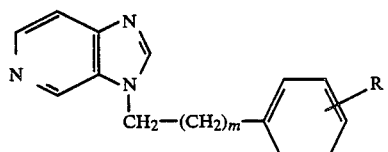

18. A compound according to claim 17 wherein R is a

group.

19. A compound according to claim 18 wherein m is 0.

20. A compound according to claim 18 wherein R¹ is ethyl.

21. A compound according to claim 18 which is ethyl 4-(3H-imidazo[4,5-c]pyridin-3-ylmethyl)benzoate.

22. A compound according to claim 18 which is ethyl 3-(3H-imidazo[4,5-c]pyridin-3-ylmethyl)benzoate.

23. A compound according to claim 17 wherein R is a

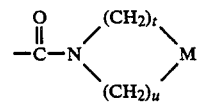

group.

24. A compound according to claim 23 wherein m is 0.

25. A compound according to claim 23 wherein M is —O—.

26. A compound according to claim 23 which is [4-(3H-imidazo[4,5-c]pyridin-3-ylmethyl)phenyl](4-morpholinyl)methanone.

27. A compound according to claim 2 having the formula

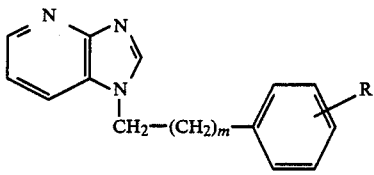

28. A compound according to claim 27 wherein R is a

group.

29. A compound according to claim 28 wherein m is 0.

30. A compound according to claim 28 wherein $R^1$ is ethyl.

31. A compound according to claim 28 which is ethyl 4-(1H-imidazo[4,5-b]pyridin-1-ylmethyl)benzoate.

32. A compound according to claim 27 wherein R is a

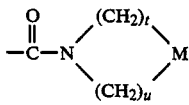

group.

33. A compound according to claim 32 wherein m is 0.

34. A compound according to claim 32 wherein M is —O—.

35. A compound according to claim 32 which is [4-(1H-imidazo[4,5-b]pyridin-1-ylmethyl)phenyl](4-morpholinyl)methanone.

36. A compound according to claim 2 having the formula

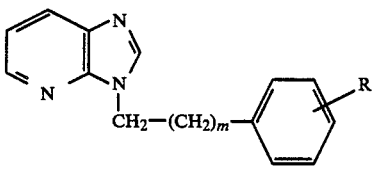

37. A compound according to claim 36 wherein R is a

group.

38. A compound according to claim 37 wherein m is 0.

39. A compound according to claim 37 wherein $R^1$ is ethyl.

40. A compound according to claim 37 which is ethyl 4-(3H-imidazo[4,5-b]pyridin-3-ylmethyl)benzoate.

41. A compound according to claim 1 having the formula

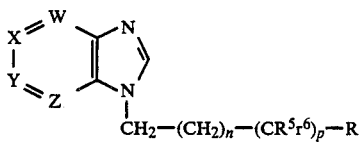

42. A compound according to claim 41 having the formula

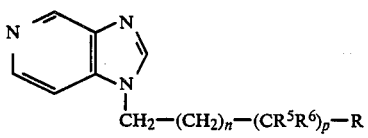

43. A compound according to claim 42 wherein n is an integer from 2 to 5 and p is 0 or 1.

44. A compound according to claim 42 wherein R is a

group.

45. A compound according to claim 44 wherein $R^1$ is ethyl.

46. A compound according to claim 44 wherein p is 0.

47. A compound according to claim 44 wherein said compound is selected from the group consisting of:
ethyl 4-(1H-imidazo[4,5-c]pyridin-1-yl)butanoate, ethyl 5-(1-H-imidazo[4,5-c]pyridin-1-yl)pentanoate,
ethyl 6-(1H-imidazo[4,5-c]pyridin-1-yl)hexanoate, and ethyl 7-(1H-imidazo[4,5-c]pyridin-1-yl)heptanoate.

48. A compound according to claim 44 wherein p is 1.

49. A compound according to claim 44 which is ethyl 2,2-dimethyl-6-(1-imidazo[4,5-c]pyridin-1-yl)hexanoate.

50. A compound according to claim 43 wherein R is a

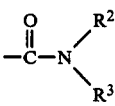

group.

51. A compound according to claim 50 wherein $R^2$ and $R^3$ are independently $C_1$–$C_8$ alkyl or $C_3$–$C_8$ cycloalkyl.

52. A compound according to claim 50 wherein p is 0.

53. A compound according to claim 50 which is N-cyclohexyl-N-methyl-7-(1H-imidazo[4,5-c]pyridin-1-yl)heptanamide.

54. A compound according to claim 43 wherein R is a

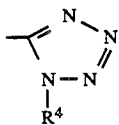

group.

55. A compound according to claim 54 wherein $R^4$ is cyclohexyl.

56. A compound according to claim 54 wherein p is 0.

57. A compound according to claim 54 wherein said compound is selected from the group consisting of:
1-[4-(1-cyclohexyl-1H-tetrazol-5-yl)butyl]-1H-imidazo[4,5-c]pyridine and
1-[5-(1-cyclohexyl-1H-tetrazol-5-yl)pentyl]-1H-imidazo[4,5-c]pyridine.

58. A compound according to claim 41 having the formula

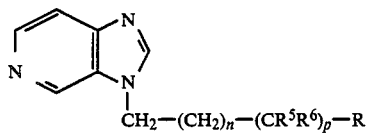

59. A compound according to claim 58 wherein n is an integer from 2 to 5 and p is 0 or 1.

60. A compound according to claim 59 wherein R is a

group.

61. A compound according to claim 60 wherein $R^1$ is ethyl.

62. A compound according to claim 60 wherein p is 0.

63. A compound according to claim 60 wherein said compound is selected from the group consisting of:
ethyl 4-(3H-imidazo[4,5-c]pyridin-3-yl)butanoate,
ethyl 5-(3H-imidazo[4,5-c]pyridin-3-yl)pentanoate,
ethyl 6-(3H-imidazo[4,5-c]pyridin-2-yl)hexanoate, and
ethyl 7-(3H-imidazo[4,5-c]pyridin-3-yl)heptanoate.

64. A compound according to claim 60 wherein p is 1.

65. A compound according to claim 60 which is ethyl 2,2-dimethyl-6-(3H-imidazo[4,5-c]pyridin-3-yl)hexanoate.

66. A compound according to claim 59 wherein R is a

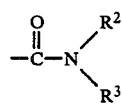

group.

67. A compound according to claim 66 wherein $R^2$ and $R^3$ are independently $C_1$–$C_8$ alkyl or $C_3$–$C_8$ cycloalkyl.

68. A compound according to claim 66 wherein p is 0.

69. A compound according to claim 66 which is N-cyclohexyl-N-methyl-7-(3H-imidazo[4,5-c]pyridin-3-yl)heptanamide.

70. A compound according to claim 59 wherein R is a

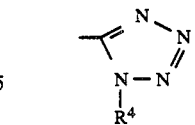

group.

71. A compound according to claim 70 wherein $R^4$ is cyclohexyl.

72. A compound according to claim 70 wherein p is 0.

73. A compound according to claim 70 which is 3-[4-(1-cyclohexyl-1H-tetrazol-5-yl)butyl]-3H-imidazo[4,5-c]pyridine.

74. A compound according to claim 41 having the formula

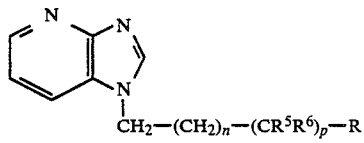

75. A compound according to claim 74 wherein n is an integer from 2 to 5 and p is 0 or 1.

76. A compound according to claim 75 wherein R is a

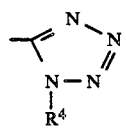

group.

77. A compound according to claim 76 wherein $R^4$ is cyclohexyl.

78. A compound according to claim 75 wherein p is 0.

79. A compound according to claim 75 which is 1-[4-(1-cyclohexyl-1H-tetrazol-5-yl)butyl]-1H-imidazo[4,5-b]pyridine.

80. A compound according to claim 41 having the formula

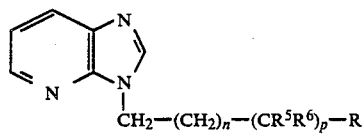

81. A compound according to claim 80 wherein n is an integer from 2 to 5 and p is 0 or 1.

82. A compound according to claim 81 wherein R is a

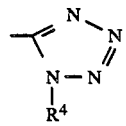

group.

83. A compound according to claim 82 wherein $R^4$ is cyclohexyl.

84. A compound according to claim 81 wherein p is 0.

85. A compound according to claim 81 which is 3-[4-(1-cyclohexyl-1H-tetrazol-5-yl)butyl]-3H-imidazo[4,5-b]pyridine.

86. A pharmaceutical composition comprising at least one compound according to claim 1, together with one or more non-toxic pharmaceutically acceptable carriers.

87. A pharmaceutical composition according to claim 86 wherein said compound is selected from the group consisting of:
ethyl 4-(1H-imidazo[4,5-c]pyridin-1-ylmethyl)benzoate,
ethyl 3-(1H-imidazo[4,5-c]pyridin-1-ylmethyl)benzoate,
ethyl 4-(3H-imidazo[4,5-c]pyridin-3-ylmethyl)benzoate,
ethyl 3-(3H-imidazo[4,5-c]pyridin-3-ylmethyl)benzoate,
ethyl 4-(1H-imidazo[4,5-b]pyridin-1-ylmethyl)benzoate,
ethyl 4-(3H-imidazo[4,5-b]pyridin-3-ylmethyl)benzoate,
N-cyclohexyl-N-methyl-4-[1H-imidazo[4,5-c]pyridin-1-ylmethyl)benzamide,
[4-(1H-imidazo[4,5-c]pyridin-1-ylmethyl)phenyl](4-morpholinyl)methanone,
[4-(3H-imidazo[4,5-c]pyridin-3-ylmethyl)phenyl](4-morpholinyl)methanone,
[4-(1H-imidazo[4,5-b]pyridin-1-ylmethyl)phenyl](4-morpholinyl)methanone,
ethyl 4-(1H-imidazo[4,5-c]pyridin-1-yl)butanoate,
ethyl 4-(3H-imidazo[4,5-c]pyridin-3-yl)butanoate,
ethyl 5-(1H-imidazo[4,5-c]pyridin-1-yl)pentanoate,
ethyl 5-(3H-imidazo[4,5-c]pyridin-3-yl)pentanoate,
ethyl 6-(1H-imidazo[4,5-c]pyridin-1-yl)hexanoate,
ethyl 6-(3H-imidazo[4,5-c]pyridin-3-yl)hexanoate,
ethyl 7-(1H-imidazo[4,5-c]pyridin-1-yl)heptanoate,
ethyl 7-(3H-imidazo[4,5-c]pyridin-3-yl)heptanoate,
ethyl 2,2-dimethyl-6-(1H-imidazo[4,5-c]pyridin-1-yl)hexanoate,
ethyl 2,2-dimethyl-6-(3H-imidazo[4,5-c]pyridin-3-yl)hexanoate,
N-cyclohexyl-N-methyl-7-(1H-imidazo[4,5-c]pyridin-1-yl)heptanamide,
N-cyclohexyl-N-methyl-7-(3H-imidazo[4,5-c]pyridin-3-yl)heptanamide,
1-[4-(1-cyclohexyl-1H-tetrazol-5-yl)butyl]-1H-imidazo[4,5-c]pyridine,
3-[4-(1-cyclohexyl-1H-tetrazol-5-yl)butyl]-3H-imidazo[4,5-c]pyridine,
1-[5-(1-cyclohexyl-1H-tetrazol-5-yl)butyl]-1H-imidazo[4,5-c]pyridine,
1-[4-(1-cyclohexyl-1H-tetrazol-5-yl)butyl]-1H-imidazo[4,5-b]pyridine, and
3-[4-(1-cyclohexyl-1H-tetrazol-5-yl)butyl]-3H-imidazo[4,5-b]pyridine.

* * * * *